(12) United States Patent
Morton (10) Patent No.: US 8,582,720 B2
(45) Date of Patent: Nov. 12, 2013

(54) TIME OF FLIGHT BACKSCATTER IMAGING SYSTEM

(75) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 220 days.

(21) Appl. No.: 12/959,356

(22) Filed: Dec. 2, 2010

(65) Prior Publication Data

US 2012/0134473 A1   May 31, 2012

Related U.S. Application Data

(60) Provisional application No. 61/266,217, filed on Dec. 3, 2009.

(51) Int. Cl.
*G01N 23/201*   (2006.01)
(52) U.S. Cl.
USPC .............................................. 378/87; 378/57
(58) Field of Classification Search
USPC ................................................ 378/57, 86, 87
See application file for complete search history.

(56) References Cited

U.S. PATENT DOCUMENTS

| | | | |
|---|---|---|---|
| 3,374,355 A | 3/1968 | Parratt et al. | |
| 5,014,293 A | 5/1991 | Boyd et al. | |
| 5,181,234 A | 1/1993 | Smith | |
| 5,202,932 A | 4/1993 | Cambier et al. | |
| 6,081,580 A | 6/2000 | Grodzins et al. | |
| 6,216,540 B1 | 4/2001 | Nelson et al. | |
| 6,418,194 B1 | 7/2002 | McPherson et al. | |
| 7,809,104 B2 * | 10/2010 | Foland | 378/57 |
| 7,860,213 B2 | 12/2010 | Akery | |

FOREIGN PATENT DOCUMENTS

US   WO 2011/069024   6/2011

OTHER PUBLICATIONS

International Search Report for PCT/US10/58809; Rapiscan Systems Inc.; Apr. 19, 2011.

* cited by examiner

*Primary Examiner* — Jurie Yun
(74) *Attorney, Agent, or Firm* — Novel IP (57) ABSTRACT

The present application discloses an X-ray imaging apparatus for determining a surface profile of an object under inspection that is positioned at a distance from the apparatus. The X-ray imaging system has an X-ray source for producing a scanning beam of X-rays directed toward the object, a detector assembly for providing a signal representative of an intensity of X-rays backscattered from the object, and processing circuitry to determine a time difference between when the X-ray source is switched on and when the backscattered X-rays arrive at the detector assembly. The processing circuitry is adapted to output data representative of the surface profile of the object under inspection.

20 Claims, 7 Drawing Sheets

TIME OF FLIGHT BACKSCATTER IMAGING SYSTEM

CROSS-REFERENCE

The present specification relies on U.S. Patent Provisional Application No. 61/266,217, filed on Dec. 3, 2009, for priority.

FIELD OF THE INVENTION

The present invention generally relates to the field of radiant energy imaging systems for detecting concealed objects, and more specifically to an X-ray backscatter system capable of measuring the surface profile of an object under inspection which can be used to produce dimensionally accurate images with an improved level of material characterization.

BACKGROUND OF THE INVENTION

Given the presently increasing threats of violence, the inspection of vehicles, including, but not limited to, luggage and cargo at transit points, has become almost universally mandatory. The screening of small and large objects is required to detect the presence of contraband such as explosives, weapons, narcotics and dangerous chemicals. Non-invasive inspection is typically achieved using X-ray scanning systems. Transmission based X-ray systems are traditionally used to inspect trucks and cargo containers, in particular when these may contain high-density materials and/or nuclear materials.

In backscatter-based systems, X-rays are used for irradiating a vehicle or object being inspected, and X-rays that are scattered back by the object are processed to provide images which help identify the presence of contraband. Typically, a backscatter imaging system utilizes a flying spot which is derived from a rotating collimator located close to a wide angle source of X-rays, such as a constant potential X-ray tube. As the collimator rotates, the resulting pencil beam of X-rays sweeps over the surface of the object to be inspected and interacts with the surface. Some of the X-rays backscatter away from the surface of the object and in the direction from which the X-rays originated. Some of the X-rays will penetrate, and pass through, the object. Those X-rays that backscatter away from the object may be captured by X-ray detectors which are located at some distance from the surface of the object. Using trigonometry, it is possible to form a one-dimensional image of the backscattered signal intensity, assuming that the surface of the object is flat. If motion is introduced between the X-ray system and the object under inspection, a two-dimensional image may then be generated In an alternative configuration, a fan beam of X-rays may be used to irradiate a whole line across the object, and a combination of collimators and detectors can be used to capture the backscatter image.

In another alternative configuration, a multi-focus X-ray source whose individual source points are arranged in a linear array may be placed behind a parallel collimator array such that each source point is constrained to irradiate only a small portion of the object under inspection. By sequencing the emission from each X-ray source point in turn, the effect of sweeping the X-ray beam across the object is generated and the resulting X-ray backscatter signal may be recorded in X-ray detectors which are located at some distance from the surface of the object. In each configuration, a constant potential X-ray source is utilized with the imaging signal being purely the magnitude of the backscattered X-ray signal at the X-ray detector.

All the above mentioned configurations of known X-ray backscatter imaging systems are based on the assumption that the objects being screened are planar or straight sided. Also, the backscatter signal has a dependence on the distance, r, which scales approximately as $1/r^4$. Therefore, in order for an X-ray backscatter system to produce a distortion-free image, the photon detector must be equidistant from all portions of the object being scanned. Thus, such systems are well-adapted for producing images of trucks or railcars, which generally have vertical sidewalls.

They are not, however, as well suited for scanning aircrafts or even cars which have oval or elliptical cross-sections because, as a collimated beam scans an oval or cylindrical surface, some portions of the scanned surface are located closer to the photon detector(s) than other portions. The variations in distance from the detector(s) produce distortions in the backscattered image. For the same reason, producing accurate and distortion-free images when screening luggage (such as on a conveyer system) and even when screening people, remains a challenge for backscatter X-ray imaging systems.

Therefore, what is needed is an inspection system that produces distortion free images for accurately determining the presence of concealed illegal materials in different types of objects, such as luggage, cargo and vehicles. Such a system should also be capable of providing both depth and material type information for an object being scanned. There is also a need for the inspection system to be mobile and non-intrusive, with an ability to work in various orientations, scanning ranges, and fields of view to suit different kinds of inspection applications.

SUMMARY OF THE INVENTION

The present invention is directed toward an X-ray imaging apparatus for determining a surface profile of an object under inspection and positioned at a distance from said apparatus, comprising an X-ray source for producing a scanning beam of X-rays directed toward said object; a detector assembly for providing a signal representative of an intensity of X-rays backscattered from said object; and processing circuitry to determine a time difference between when the X-ray source is switched on and when the backscattered X-rays arrive at the detector assembly and to output data representative of the surface profile of the object under inspection.

Optionally, the minimum distance between the apparatus and the object under inspection is 100 mm. The maximum distance between the apparatus and the object under inspection is 5 m. The X-ray source is pulsed such that the duration of the X-ray beam being on is in the range of 1 μs to 100 μs and a duration of the X-ray being off is in the range of 1 μs to 100 μs. The duration of the X-ray beam on time and off time is each less than 1 ns. The X-ray imaging apparatus is mounted on a vehicle which is adapted to be driven past the object under inspection. The X-ray imaging apparatus is mounted on a vehicle that is adapted to be driven to an inspection site and kept stationary while the object under inspection passes the vehicle.

In another embodiment, the present invention is directed toward an X-ray imaging apparatus for determining the presence and location of a threat beneath the exterior surface of an object under inspection, comprising: an X-ray source for producing a scanning pencil beam of X-rays directed toward said object; a detector assembly for providing a first signal representative of the intensity of the X-rays backscattered from said exterior surface of the object under inspection and a second signal representative of the intensity of the X-rays backscattered from said threat beneath the exterior surface of the object under inspection; and processing circuitry to determine a first time difference between when the X-ray source is switched on and when the X-rays backscattered from the exterior surface of the object under inspection arrive at the detector assembly and a second time difference between when the X-ray source is switched on and when the X-rays backscattered from the threat beneath the exterior surface of the object under inspection arrive at the detector assembly and to output data representative of the surface profile of the object under inspection based upon at least one of said first time difference or second time difference.

Optionally, the minimum distance between the apparatus and the object under inspection is 100 mm. The maximum distance between the apparatus and the object under inspection is 5 m. The X-ray source is pulsed such that a duration of the X-ray beam being on is in the range of 1 µs to 100 µs and a duration of the X-ray being off is in the range of 1 µs to 100 µs. The duration of the X-ray beam on time and off time is each less than 1 ns. The X-ray imaging apparatus is mounted on a vehicle which is adapted to be driven past the object under inspection. The X-ray imaging apparatus is mounted on a vehicle that is adapted to be driven to an inspection site and kept stationary while the object under inspection passes the vehicle.

In another embodiment, the present invention is directed toward determining a surface profile of an object under inspection, said method comprising the steps of positioning an object under inspection at a distance from an X-ray imaging apparatus, wherein said X-ray imaging apparatus comprises an X-ray source and a detector array; operating said X-ray source to produce a scanning pencil beam of X-rays directed toward said object; detecting a signal representative of the intensity of the X-rays backscattered from said object, using said detector array; determining the time difference between when the X-ray source is switched on and when the backscattered signal is detected; and outputting data representative of the surface profile of the object under inspection.

Optionally, the object under inspection is positioned no closer than 100 mm and no farther than 5 m from the X-ray imaging apparatus. The X-ray source is kept on for no less than 1 µs and no more than 100 µs and is kept off for no less than 1 µs and no more than 100 µs. The X-ray source is kept on for less than 1 ns and kept off for less than 1 ns.

In another embodiment, the present invention is directed toward a portal gantry having a top side, left side, and right side, comprising the X-ray imaging apparatus of claim 1. The portal X-ray imaging apparatus is integrated into at least two of the top side, left side, or right side.

These and other embodiments shall be described in greater detail in the Detailed Description when read in light of the Figures.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

The present invention is a time of flight backscatter system which uses the finite velocity of the X-ray signal to determine the distance from the X-ray source to the surface of the object such that the surface profile of the object may be determined.

The system of present invention provides an accurate spatial representation of backscattering from the object to be scanned and eliminates the assumption of straight sided objects on which conventional X-ray backscatter imaging systems are based. Knowledge of the surface profile provides a further inspection result which may be used to verify the integrity of the object under inspection.

Although one embodiment of the present invention is described with reference to X-ray scanning, one of ordinary skill in the art would appreciate that object screening may be performed using any available radiation imaging technique such as, but not limited to X-ray scattering, infrared imaging, millimeterwave imaging, RF imaging, radar imaging, holographic imaging, CT imaging, and MRI. Any imaging system that has the potential for displaying object detail may be employed.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
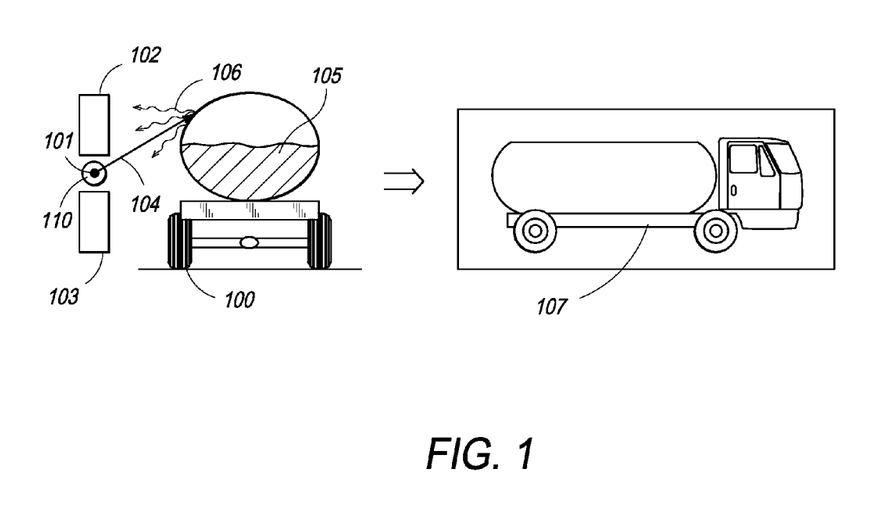
FIG. 1 illustrates a backscatter X-ray imaging system.

FIG. 1 illustrates a conventional backscatter X-ray imaging system 100. Referring to FIG. 1, the system 100 comprises an X-ray tube 101 with a rotating collimator assembly 110 and two large area backscatter imaging sensors 102 and 103. A scanning pencil beam of X-rays 104 is emitted towards an object 105. The pencil beam 104 is obtained by rotating the collimating disk 110 around a constant potential X-ray source (X-ray tube 101). As the beam 104 scans across the object 105 to be inspected, a fraction of the X-rays backscatter away from the surface of the object and towards one or more X-ray detectors. In this manner, a backscatter signal 106 is generated, which is sensed by the detectors 102 and 103. Knowing the angle of the X-ray pencil beam with respect to a fixed plane and the distance to the surface of the object under inspection from the X-ray source point and detectors, it is possible to reconstruct a backscatter X-ray image. An exemplary X-ray backscatter image 107 for the object 105 is shown in FIG. 1.

One of ordinary skill in the art would note that the distances between the surface of the object and the planar detector arrays are variable, since the object is not straight sided. Further, since the distance from the X-ray source to the object under inspection is not known in general, an assumption is generally made that the object is planar and at a fixed distance from the source. Thus, if the object is closer than assumed, then the object will appear smaller in the image and conversely, if the object is further away then it will appear to be larger. The result is an image which is representative of the object under inspection but not with correct geometry. This makes it difficult to identify the precise location of a threat or illicit object within the object under inspection.

The present invention addresses the above problem by integrating time of flight processing into conventional backscatter imaging. X-rays travel at a constant speed which is equal to the speed of light ($3 \times 10^8$ m/s). An X-ray will therefore travel a distance of 1 m in 3.3 ns or equivalently, in 1 ns ($10^{-9}$ s) an X-ray will travel 0.3 m. Thus, if the distance between a backscatter source and the object under inspection is on the order of 1 m, it corresponds to around 3 ns of transit time. Similarly, if the backscatter X-ray detector is also located around 1 m from the surface of the object, it corresponds to an additional 3 ns of transit time. Thus, the signal received at the detector should be received, in this example, 6 ns after the X-ray beam started its transit from the X-ray tube. In sum, the X-ray's transit time is directly related to the detectors' distance to or from the object. Such times, although quite short, can be measured using detection circuits known to those of ordinary skill in the art.

The minimum distance is practically associated with the time resolution of the system. Objects can be proximate to the source, but one will not see much scattered signal since the scatter will generally be directed back to the X-ray source rather than to a detector. A practical lower limit, or the minimum distance between the plane of the system and the nearest part of the object to be inspected, is 100 mm. The further away the object is from the detector, the smaller the signal size and thus a practical upper limit for distance is of the order of 5 m.

Figure 2A:
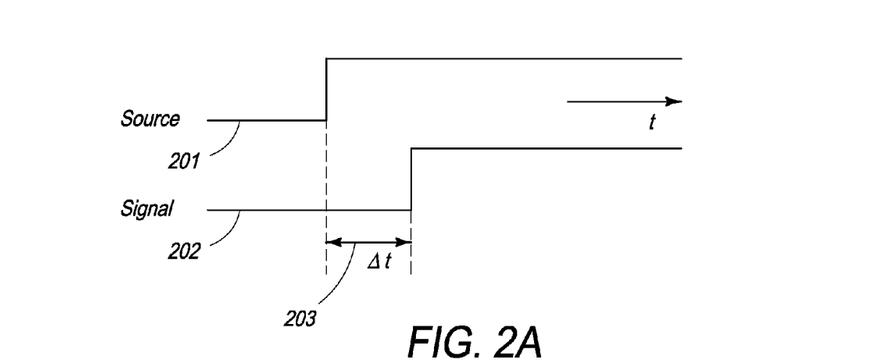
FIG. 2*a* depicts a representation, as a step function, of an X-ray source being switched rapidly from its beam-off condition to its beam-on condition.
Figure 2B:
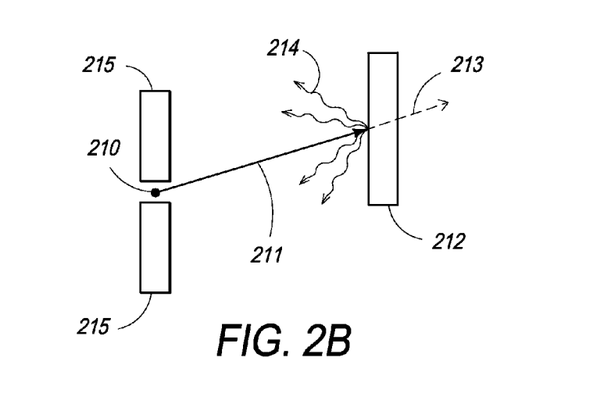
FIG. 2*b* diagrammatically illustrates an operation of time of flight backscatter imaging.

In the system of present invention, as shown diagrammatically in FIGS. 2a and 2b, the distance between the X-ray source and the object under inspection is determined precisely by recording the time taken for an X-ray to leave the source and reach the detector. FIG. 2a depicts a representation, as a step function, of an X-ray source being switched rapidly from its beam-off condition to its beam-on condition. While 201 represents the step function at the source, 202 represents the detector's response. Thus, as can be seen from 201 and 202, after the beam is switched on from its off state at the source, the detector responds with a step-function like response after a time delay At 203. Referring to FIG. 2b, as the source 210 emits a pencil beam 211 of X-rays towards the object 212, some of the X-rays 213 transmit into the object 212, while some X-rays 214 backscatter towards the detectors 215.

It may be noted that there are different path lengths from the X-ray interaction point (with the object) to the X-ray detector array. Therefore if a large detector is used, there will be a blurring to the start of the step pulse at the detector, where the leading edge of the start of the pulse will be due to signal from the part of the detector which is nearest to the interaction spot, and the trailing edge of the start of the pulse will be due to signal from parts of the detector which are further away from the interaction spot. A practical system can mitigate such temporal blurring effects by segmenting the detector such that each detector sees only a small blurring and the changes in response time each provide further enhancement in localisation of the precise interaction position, hence improving the determination of the surface profile of the object under inspection.

The detector size (minimum and/or maximum) that would avoid such blurring effects described above is commensurate with the time resolution of the system. Thus, a system with 0.1 ns time resolution has detectors of the order of 50 mm in size. A system with 1 ns time resolution has detectors of the order of 500 mm in size. Of course, smaller detectors can be used to improve statistical accuracy in the time measurement, but at the expense of reduced numbers of X-ray photons in the intensity signal, so there is a trade-off in a practical system design which is generally constrained by the product of source brightness and scanning collimator diameter.

Ideally, for best time of flight data, the spatial resolution should be reduced (i.e. large area of irradiation) and combined with a bright X-ray source to give best measurement accuracy. In one embodiment, a reasonable trade-off is an irradiation diameter in the range of 5 mm and 10 mm at the surface of the object with an X-ray beam current in the range of 5 mA to 20 mA with 0.5 ns time resolution and detector size of around 200 mm square per sub-panel.

In general, spatial resolution depends on the sweep speed of the flying spot and on the design of the collimator used—the better the spatial resolution, the worse the statistical noise in the image data for constant X-ray source brightness. Generally, it is practical to design a system with spatial resolution in the range of 1 mm to 20 mm full-width-at-half-maximum of the irradiating spot, but this size is dependent on the distance from the source to the surface of the object, so a slightly complicated relationship. In principle, depth resolution and spatial resolution are independent but in practice they are associated through practical constraints in X-ray source brightness.

Figure 3A:
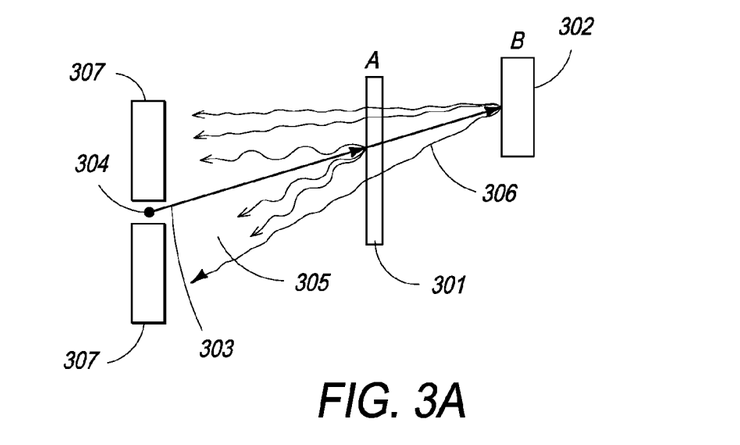
FIG. 3*a* illustrates diagrammatically the determination of a depth profile component of the signal using the time of flight backscatter system of the present invention.
Figure 3B:
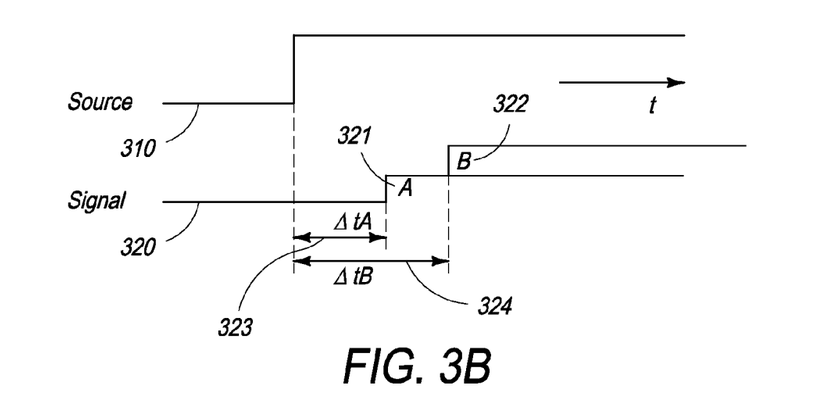
FIG. 3*b* illustrates the step function at source and detector response when the detectors sense two signals corresponding to one object being beneath another object.

The time of flight backscatter system of the present invention is also used to determine the depth profile component of the signal, which, in turn, is used to establish the presence and location of any threat objects beneath the exterior surface of an object being scanned. This is shown in FIGS. 3a and 3b. Referring to FIG. 3a, object A 301 is the primary object being scanned, and another object B 302 is located under the surface of the object A 301. This is representative, for example, of a package of goods (object B) placed within a cargo container (object A) with a metal skin. For the purpose of clarity, the second object B 302 is shown beside the object A 301. A pencil beam 303 of X-rays is emitted from the source 304 and illuminates object A 301. Some of the X-rays 305 are backscattered from object A 301, while some radiation is transmitted through object A 301 to illuminate object B 302. Rays 306 are also backscattered from object B 302. In this case, the detectors 307 will sense two distinct signals, one at a first time due to the metal skin on the surface of the object A 301, and a further signal at a second time due to the package of goods (object B 302) located beneath the surface.

FIG. 3b illustrates the step function 310 at the source and the detector response 320 when the detectors sense two signals corresponding to one object being beneath another object. The two signals at the detector are represented by A 321 and B 322. While pulse A 321 starts after a time delay of $\Delta t_A$ 323 after the source is turned on, pulse B 322 starts after a time delay of $\Delta t_B$ 324. These two different signals may then be interpreted in order to determine the exact location of an object within the object under inspection. For example, such additional information may be used to determine if the object B 302 in FIG. 3a is situated within a hidden compartment in the wall of the container (object A 301) or whether it is located within the normal storage area of the container.

Depth resolution is dependent on the speed of the electronics and the switch-on time of the source. A 1 ns time resolution will give depth resolution of the order of 100 mm, while a 0.5 ns time resolution will give depth resolution of the order of 50 mm.

It is known in the art that the backscatter signal intensity falls off rapidly with distance into the object and with the presence of overlying structures. However, the time of flight backscatter signal as used in the present invention enables a system to determine the presence of weakly scattering signals in the presence of highly scattering signals through analysis of the leading edge of the time of flight signal. Thus, the present method provides an opportunity for deeper inspection into the object as compared to existing backscatter systems, where only the total backscatter signal is measured and hence small signals from deeper objects are obscured by the larger signal from nearer objects.

Figure 4:
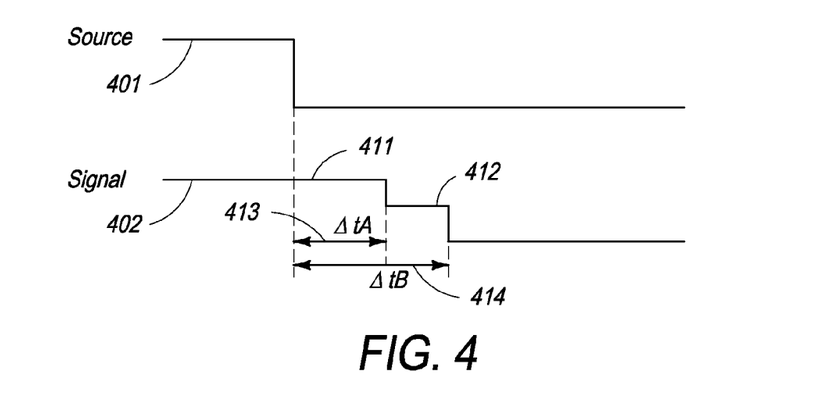
FIG. 4 illustrates graphically how the time of flight backscatter imaging signal may be collected when the X-ray beam is switched off.

One of ordinary skill in the art would appreciate that the time of flight backscatter signal also exists at the time when the X-ray beam is switched off. This is shown diagrammatically in FIG. 4. FIG. 4 illustrates the step function at the source 401 and the step function corresponding to the backscatter signal collected at the detector 402 when the X-ray beam is switched off. For the purpose of step function response, the objects shown in FIG. 3 (A 310 and B 302) are considered. Thus the detector signal again comprises two step pulses 411 and 412 corresponding to two objects. While the end of pulse 411 starts after a time delay of $\Delta t_A$ 413 after the source is turned off, the end of pulse 412 starts after a time delay of $\Delta t_B$ 414.

It is therefore possible to improve the accuracy of the time of flight backscatter signal by recording the profile of the detected signal at beam switch on and again at beam switch off.

Figure 5:
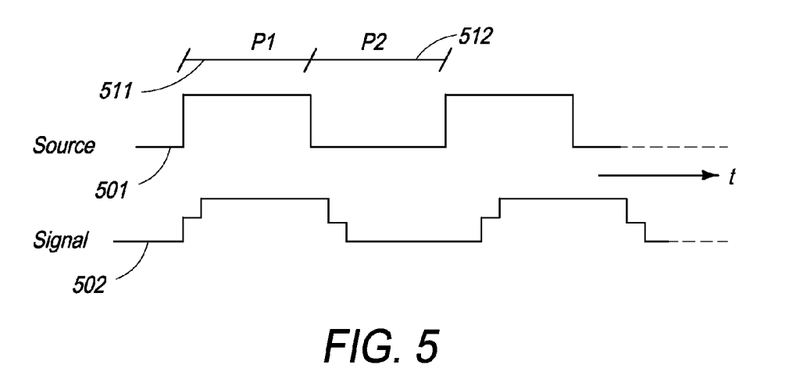
FIG. 5 illustrates graphically how the signal-to-noise ratio in the time of flight measurement may be improved by using X-ray pulse sequences.

According to an aspect of the present invention, the signal-to-noise ratio in the time of flight measurement is further improved by using X-ray pulse sequences. This is shown in FIG. 5. Referring to FIG. 5, a rapid sequence of pulses 501 is provided by the source (X-ray tube). The duration of the beam on phase (P1) 511 and beam off phase (P2) 512 for each pulse is selected to accommodate electronics data acquisition system bandwidth and according to X-ray tube target loading capacity. In one embodiment for example, the duration of beam on and off phases, P1 511 and P2 512 respectively, are optimized to be in the range 1 μs to 100 μs. Also in one embodiment, the pulsed X-ray source is capable of rapid turn on and turn off times. As an example, the X-ray source delivers pulses with a beam turn on and beam turn off time of less than 1 ns each. The detector response is illustrated by 502 in FIG. 5, and it represents for the backscatter signal sensed in response to the sequences of pulses 501 generated by the source.

Figure 6:
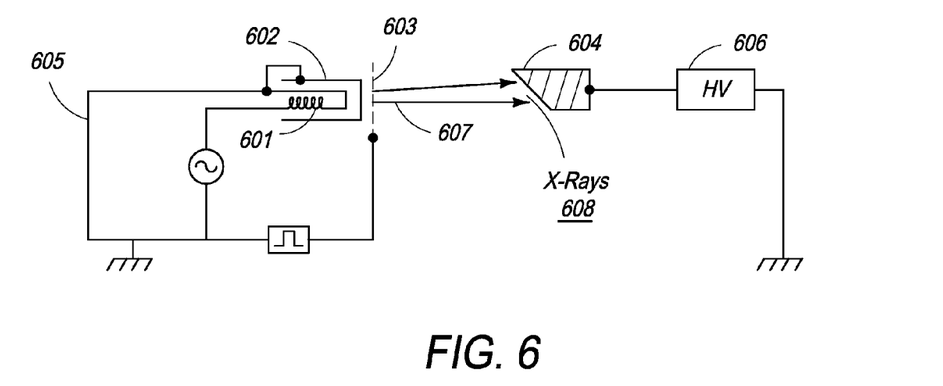
FIG. 6 shows an exemplary pulsed X-ray tube design that uses an electrostatic grid to control the pulsing of the X-ray output.

FIG. 6 illustrates an example of a suitable X-ray tube configuration for delivering pulsed X-rays. In one embodiment, a pulsed X-ray tube design that uses an electrostatic grid to control the pulsing of the X-ray output is employed. Referring to FIG. 6, a thermionic electron gun 601 is fitted with a grid 602 in close proximity to the electron emitting surface 603. In this configuration, the electron gun 601 can be operated in a space charge limited mode such that the actual grid voltage is only weakly related to the delivered tube current. By keeping the grid 602 in close proximity to the gun 601, the switching voltage that is required to turn the beam on and off may be kept at quite a low value, and generally below 100V. By making the grid elements very thin, for example by using a crucifix grid with 100-300 um wide elements, the capacitance of the grid is kept to a low value, thereby improving the grid drive circuit performance. A high speed switching circuit can then be used to switch the grid with nanosecond turn on and turn off times. The grid 602 is thus used to provide a pulsed electron beam 607 which modulates the X-ray output 608. The anode 604 is held at a positive high voltage with respect to the cathode 605 at ground potential. In one embodiment, the high voltage 606 is in the range of 120 kV to 320 kV.

Figure 7:
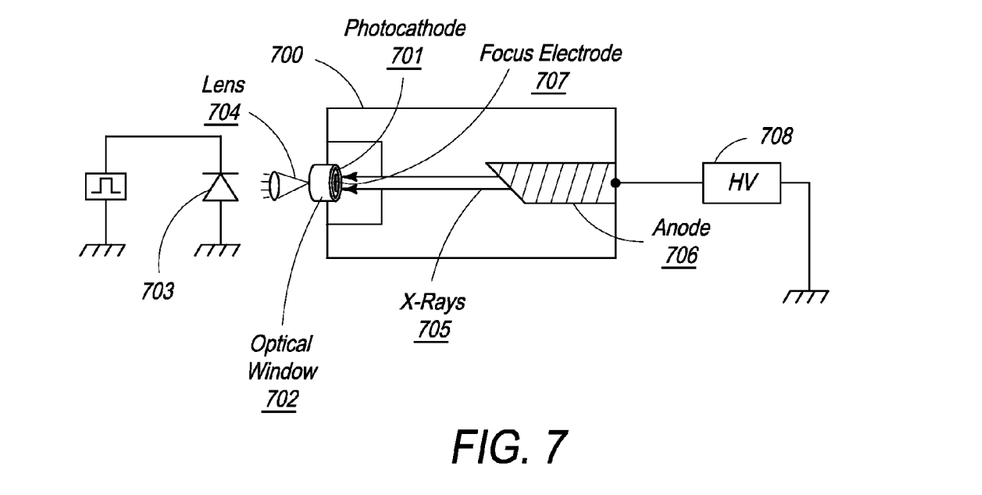
FIG. 7 shows an exemplary pulsed X-ray tube design that uses a photocathode to provide a pulsed electron beam which modulates the X-ray output.

An alternative X-ray tube configuration is shown in FIG. 7. This configuration uses a photocathode to provide a pulsed electron beam which modulates the X-ray output. Referring to FIG. 7, photocathode 701 is deposited onto an optically transparent window 702, which may be comprised of, for example, a quartz or sapphire element. A pulsed optical system, comprising a light emitting diode 703 and a lens 704, is focused onto the photocathode 701 through the window 702. As the optical system pulses, the photocathode emits electrons 705. By placing an anode 706 at high potential (HV 708) with respect to the photocathode 701, electrons 705 from the photocathode will be accelerated to the anode 706, thereby forming an X-ray signal. A suitable electrostatic focusing system 707 is also provided to control the electron trajectories within the tube 700. In this case, the output pulse from the tube 700 is determined almost completely by the pulse characteristics of the optical system. Those skilled in the art would recognise that contemporary optical systems are capable of sub-nanosecond pulsing in compact configurations with reliable components.

One of ordinary skill in the art would also appreciate that alternate X-ray tube configurations can be designed and the configurations described above with reference to FIGS. 6 and 7 are representative examples of suitable X-ray tube designs. It should also be recognized by persons of ordinary skill in the art that alternate X-ray sources such a pulsed electron accelerators or high power laser sources may be used in place of high voltage X-ray tubes.

Figure 8:
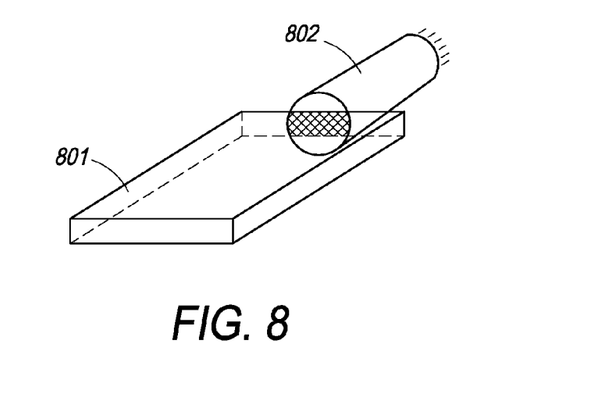
FIG. 8 illustrates an exemplary high speed backscatter detector module for measurement of the time of flight backscatter signal.

In order to record the time of flight backscatter signal, a high speed X-ray detector is required. FIG. 8 shows one example of a high speed backscatter detector module for measurement of the time of flight backscatter signal. Referring to FIG. 8, in this configuration a sheet of scintillation material 801, such as a plastic scintillator with fast rise time, is optically coupled to a high speed photodetector 802 such as a photomultiplier tube. As X-rays interact in the detector 802, light photons are generated and a fraction of these light photons transport to the detector through reflection and are scattered from the surfaces of the sheet of scintillator material 801. Since an optical photon needs to travel a finite distance through the scintillator material and there is also a finite transit time for a pulse through the photodetector, it results in the detector having a characteristic response time. One of ordinary skill in the art would appreciate that these are constant effects and may be calibrated out from the measured data in a straightforward fashion. In one embodiment, an exemplary detector is designed with an area ranging from 100×100 mm to 300×500 mm, depending on the performance requirement of the system and the overall cost of the system.

Figure 9A:
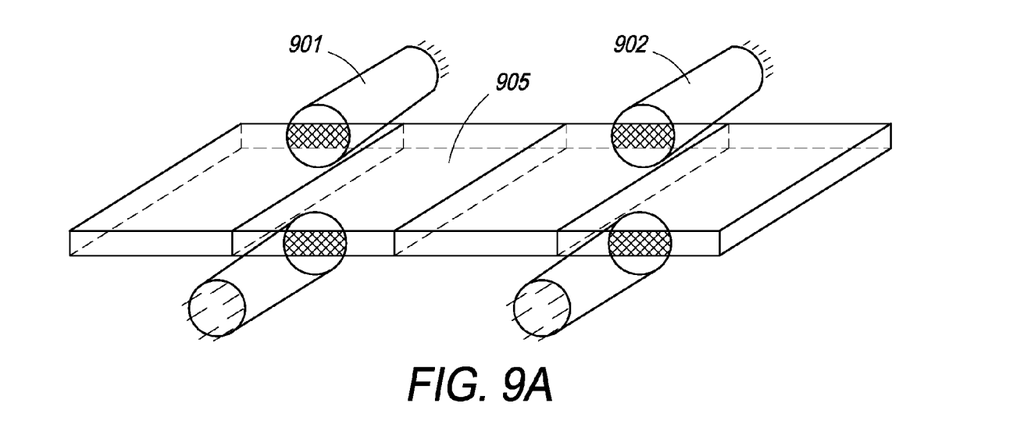
FIG. 9*a* illustrates a first exemplary arrangement for using an array of high speed backscatter imaging modules to improve overall detection efficiency and area coverage of the time of flight backscatter imaging system.

To mitigate against the effect of finite transit time of the optical photons through the scintillation material, it is advantageous to fabricate a large area detector from a series of smaller area detectors. One example of how this can be achieved is shown in FIG. 9a. Referring to FIG. 9a, smaller detector elements 901, 902 similar to the detector 802 shown in FIG. 8 are stacked together to form a larger detector assembly. All the detector elements 901, 902 are optically coupled to a common sheet 905 of scintillator material. Alternatively, the detector elements may be individually coupled to sheets of scintillator material.

Figure 9B:
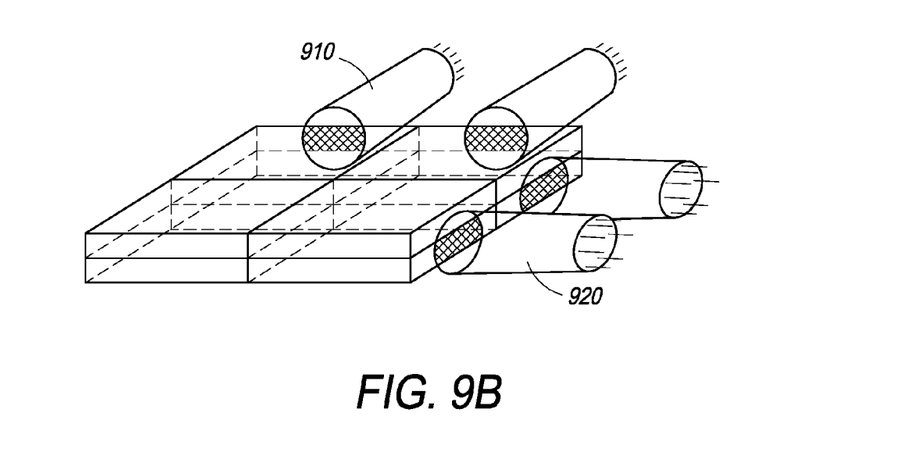
FIG. 9*b* illustrates a second exemplary arrangement for using an array of high speed backscatter imaging modules to improve overall detection efficiency and area coverage of the time of flight backscatter imaging system.

Another alternative configuration for employing an array of detectors is shown FIG. 9b. Referring to FIG. 9b, two sets of rectangular detectors 910, 920 are situated in orthogonal directions. By analysing the signals from the detector set in coincidence, further information about the interaction point of the X-ray beam with the object can be inferred. Thus, using an array of high speed backscatter imaging modules improves the overall detection efficiency and area coverage of the time of flight backscatter imaging system.

One of ordinary skill in the art would appreciate that alternate detector materials and detector configurations could be selected for use in a time of flight backscatter imaging system and the examples shown in FIGS. 8, 9a and 9b should be considered as being representative only.

Figure 10:
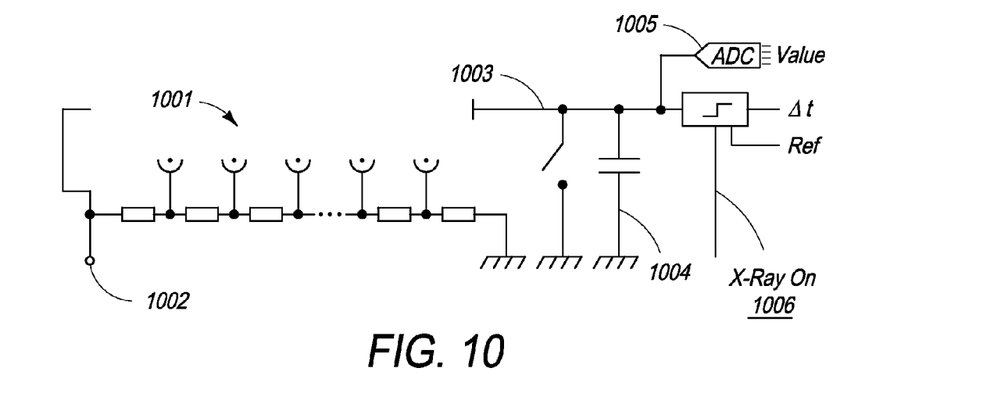
FIG. 10 illustrates an exemplary photodetector circuit based on a photomultiplier tube, as used with the time of flight backscatter imaging system of present invention.

FIG. 10 shows an exemplary electronic circuit that is used in the X-ray backscatter system of the present invention to read out the signal from the photomultiplier tube detector. The circuit shown in FIG. 10 is a low cost, primarily analog circuit that reads out the detected signal. Referring to FIG. 10, the photomultplier tube 1001 is operated with a negative cathode 1002. The anode 1003 is connected directly to a capacitor 1004. Current passing through this capacitor 1004 as a result of optical photon arrival at the photocathode 1002 will integrate resulting in the formation of a voltage across the capacitor 1004. An ADC (analog to digital converter) 1005 is provided to read this voltage in order to determine the total signal recorded during a pulse and this is the equivalent to the standard X-ray backscatter imaging signal. This photodetector circuit provides both the magnitude of the conventional backscatter signal and the additional time of flight backscatter signal 1006.

Figure 11:
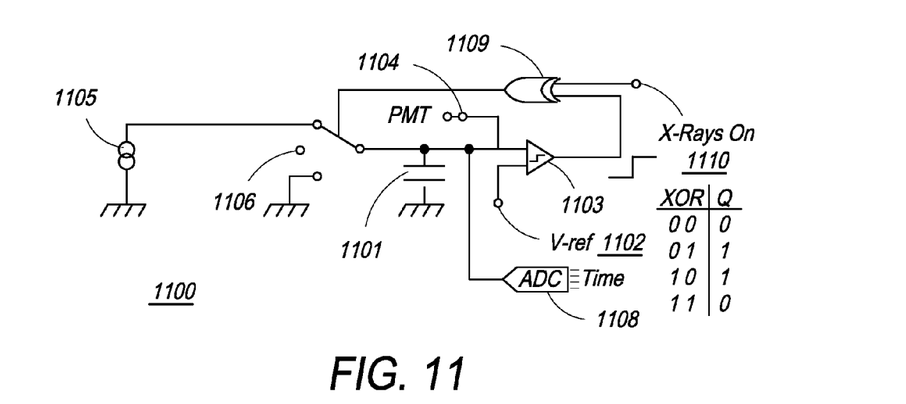
FIG. 11 illustrates an exemplary time-to-digital circuit for recording the difference between the time that X-ray tube was switched on and the time that the backscattered signal arrives at the detector.

FIG. 11 illustrates another exemplary circuit that can be used for recording the time difference between when the X-ray tube was switched on and when the backscattered signal arrives at the detector. Referring to FIG. 11, the time-to-digital circuit 1100 compares the voltage on the capacitor 1101 against a threshold reference voltage $V_{ref}$ 1102. When the voltage across the capacitor and the reference voltage become equal, a digital value is produced that is proportional to the time delay between the X-ray source turning on and the detector signal being received. This is the time of flight backscatter imaging signal described above with reference to FIGS. 2a and 2b. As shown schematically in FIG. 11, the comparator circuit comprises two parts: (1) a comparator 1103 which compares the photomultiplier charging capacitor voltage, $V_{PMT}$ 1104, and a known reference voltage $V_{ref}$ 1102 and (2) a constant current source 1105, a three-position switch 1106, capacitor 1101 and an analog to digital converter 1108. The output of the comparator 1103 is fed to an XOR gate 1109, whose other input is the X-ray on signal 1110.

As soon as the X-ray beam is turned on (X-Rays-On 1110 is activated), the three position switch 1106 is moved from its ground connected position to connect to the output of the constant current source 1105. This begins charging up the comparator capacitor 1101. The comparator capacitor 1101 continues to charge up as long as $V_{PMT}$ 1104 is lower than the reference voltage $V_{ref}$ 1102. As soon as $V_{PMT}$ 1104 equals or exceeds the reference voltage $V_{ref}$ 1102, the three position switch 1106 is rotated to the disconnected position and the voltage is maintained on the comparator capacitor 1101. At this point the voltage is sampled by the analog to digital converter 1108 and the resulting digital value is thus directly proportional to the time difference between the X-ray beam turning on and the backscattered X-ray signal being received at the detector. Once the analog to digital conversion is completed, the three position switch 1106 is connected to the ground position in order to discharge the capacitor 1101 and prepare for the next pulse.

As an extension of the above circuit, it is possible to time digitize the rising edge of the pulse by using multiple copies of the comparator circuit of FIG. 11. This technique is shown in schematically in FIG. 12, and may be used for recording depth profile information, as described earlier with reference to FIGS. 3a and 3b.

Figure 12:
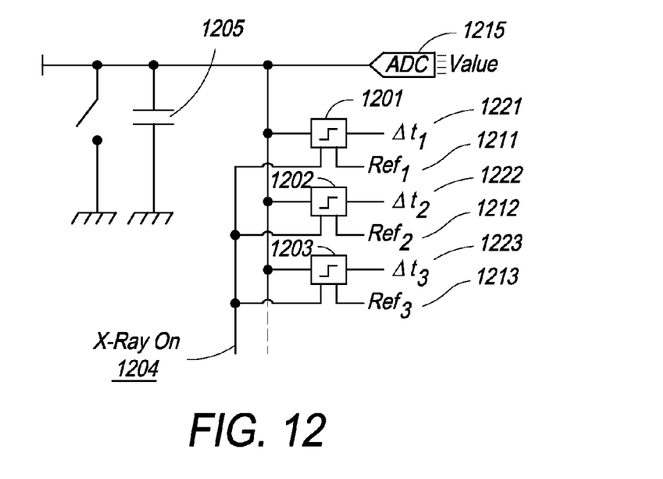
FIG. 12 illustrates an exemplary circuit that uses time of flight backscatter signal for recording depth profile information.

Referring to FIG. 12, a plurality of comparator circuits 1201, 1202 and 1203 are connected to the X-ray on signal 1204. As the second input, reference voltages Ref1 1211, Ref2 1212 and Ref3 1213 are fed to comparator circuits 1201, 1202 and 1203 respectively. The voltage across the capacitor 1205 is sampled by the analog to digital converter 1215, and the resulting digital value is directly proportional to the time difference between the X-ray beam turning on and the backscattered X-ray signal being received at the detector. In cases where there are multiple objects hidden beneath a given object, the plurality of comparator circuits 1201, 1202 and 1203 produce signals at different time intervals represented by $\Delta t_1$ 1221, $\Delta t_2$ 1222, and $\Delta t_3$ 1223 respectively. This provides a means to collect the depth profile information. That is, the different signals produced by the comparator circuits may be interpreted in order to determine the exact location of an object within the object under inspection.

One of ordinary skill in the art would appreciate that there are many ways in which the data required for time of flight backscatter imaging may be collected, and that the circuits described in FIGS. 11 and 12 represent exemplary approaches. Many other approaches are possible, including high speed digitization at the anode output of the photomultiplier tube and the use of multiple ADCs, each triggered at a time offset to the others.

Figure 13A:
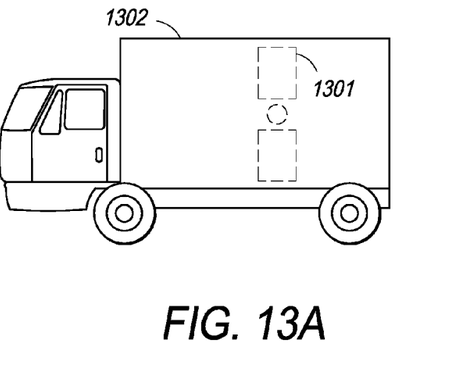
FIG. 13*a* illustrates an exemplary application of the time of flight backscatter imaging system of the present invention on a mobile scanning platform.
Figure 13B:
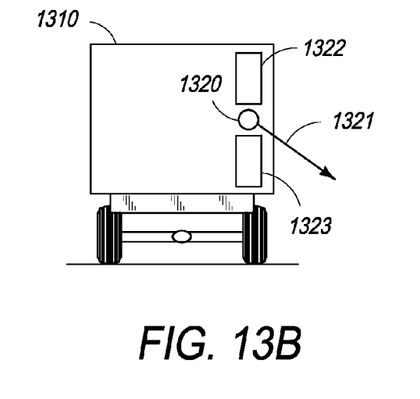
FIG. 13*b* illustrates another exemplary application of the time of flight backscatter imaging system of the present invention on a mobile scanning platform.

In one embodiment of the time of flight backscatter imaging system of the present invention, the detection system may be mounted on a mobile platform. Such an exemplary imaging system is shown in FIGS. 13a and 13b. Referring to FIG. 13a, an X-ray apparatus 1301 is installed in a vehicle 1302 that can be driven past stationary targets at a known velocity. As the vehicle drives by, time of flight backscatter data is collected in order to form a two-dimensional image. In another embodiment, shown in FIG. 13b, the X-ray vehicle 1310 is driven to a location, such as a roadside, and the time of flight backscatter 1320 system is activated. The backscatter imaging system 1320 further comprises the X-ray source 1321 and two large area detectors 1322 an 1323. In one embodiment, one or more sensors (not shown) that are located on the X-ray vehicle determine the presence of a passing object to be scanned, such as a passing vehicle, and the time of flight backscatter system 1320 is turned on automatically. In one embodiment, speed sensors (not shown), such as a scanning laser beam or a radar sensor, determine the speed of the passing vehicle and the two dimensional image is formed. Once the vehicle has been scanned, the X-ray apparatus 1320 is turned off automatically. Once scanning at a given location is completed, the vehicle 1310 can simply be driven to a new location and scanning can recommence as required. This feature provides the capability for random location scanning in a reasonably covert manner.

In a further embodiment of the present invention, a time of flight backscatter system is combined with a high energy transmission X-ray imaging system to improve clarity and accuracy in imaging. Advantageously, the high energy transmission imaging system will be operated using a pulsed linear accelerator source in which case the high energy transmission imaging pulse is active typically for only a few microseconds at a time. In one embodiment, the rotation of the flying spot collimator for the time of flight backscatter system is controlled such that the flying spot is not interacting with the object during the high energy pulse to ensure that there is no cross talk between the high energy and time of flight backscatter imaging systems.

Figure 14:
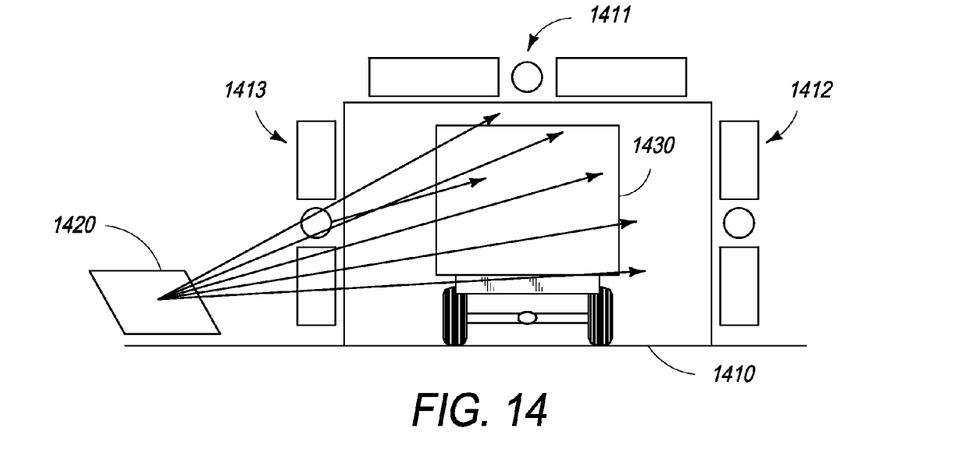
FIG. 14 illustrates an exemplary configuration, wherein the time of flight backscatter imaging system of the present invention is used along with a high energy transmission X-ray inspection system.

FIG. 14 illustrates a schematic diagram of a time of flight backscatter imaging system 1410 in partnership with a high energy transmission X-ray inspection system 1420. Referring to FIG. 14, the time of flight backscatter imaging system 1410 comprises a plurality of time of flight imaging sensors 1411, 1412 and 1413, which can be located on multiple sides of the object 1430 under inspection. This improves coverage of the time of flight backscatter inspection. A person skilled in the art would understand that the time of flight backscatter system 1410 should be offset in the scan direction from the high energy transmission imaging beam 1420 to simplify system assembly. The combined high energy transmission and time of flight backscatter system may be configured in any of a plurality of arrangements based on the requirement of application, such as but not limited to, on a mobile platform, on a stationary drive through portal gantry or rail scanner, on a scanning gantry system mounted on rails or with any other cargo motion system such as a platen system or roller bed conveyor.

Figure 15:
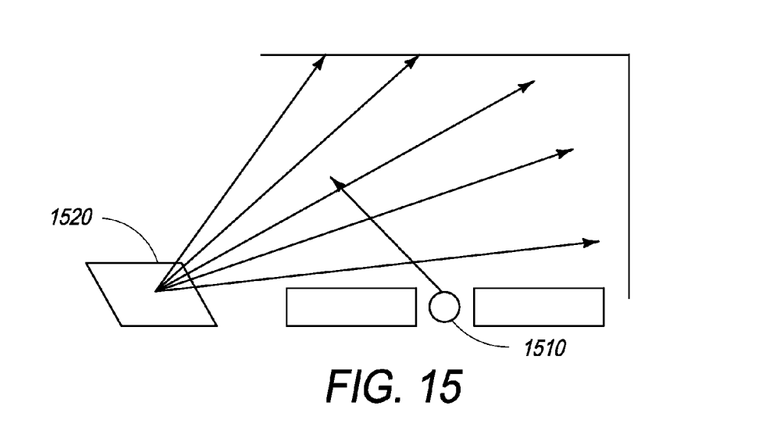
FIG. 15 illustrates an exemplary application of the time of flight backscatter imaging system, where it can be used for imaging the underside of vehicles.

In a further embodiment of the present invention, as shown in FIG. 15, the time of flight backscatter system 1510 is combined with a transmission X-ray screening system 1520. This arrangement can be advantageously used to inspect the underside of vehicles as they are driven past as well as objects on a conveyor system.

Figure 16:
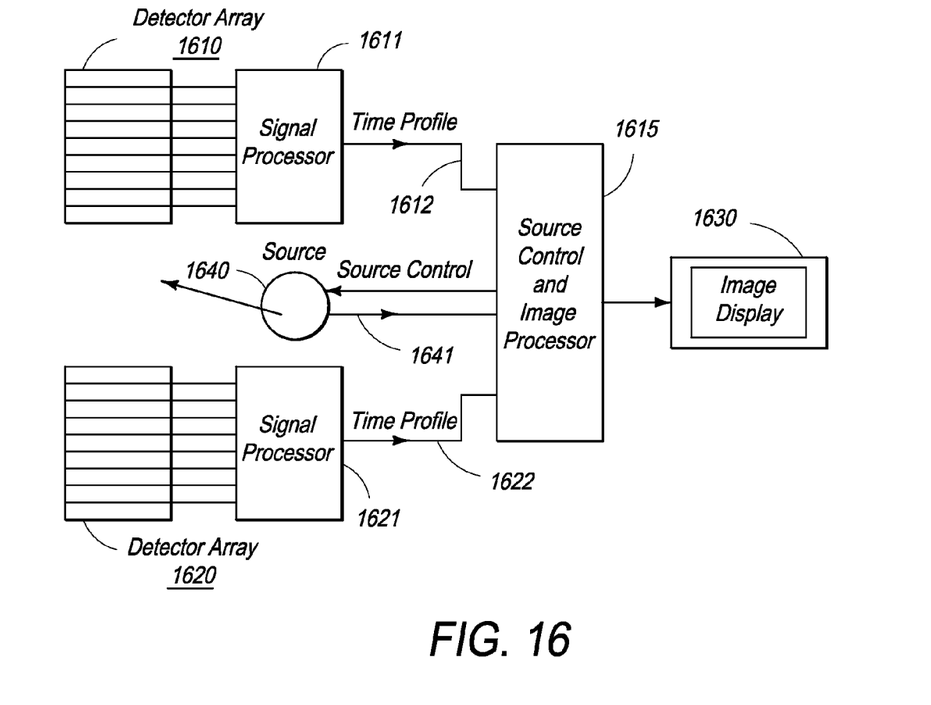
FIG. 16 illustrates an exemplary configuration data acquisition system for collecting time of flight backscatter imaging signals and representing them on a display.

FIG. 16 illustrates diagrammatically exemplary electronics and control systems employed by the system of present invention in order to process data from the detectors and to synchronize the acquisition of data with the operation of the source. Referring to FIG. 16, in order to maximize accuracy in the location of the origin of each scatter signal, two groups of segmented detectors 1610 and 1620 are shown. One of ordinary skill in the art would appreciate that any number of groups of detectors may be used, depending upon the requirements of clarity and accuracy of imaging in a given application. Each group of detectors 1610, 1620 are connected to signal processor units 1611 and 1621, respectively. The signal processor units 1611 and 1621 combine the information from the respective detector to determine the most likely interaction spot, from where the X-rays are backscattered from the object under inspection. This is done by analyzing the time domain data from each detector for each X-ray pulse and then "centroiding" this to determine the exact location of the interaction site. "Centroiding" refers to taking a geometric mean of a set of measurements. In this case, the measurements are of position, and the idea is to combine the multiple measurements together to get an average distance based on the set of independent measurements. The signals 1612, 1622 corresponding to corrected time profile and exact interaction site are then passed by the processors 1611 and 1621 respectively on to a system control and image processing block 1615. The image processing block 1615 then generates and renders the final output image on a display 1630. The system control block 1615 also controls the X-ray source 1640, via the source control signals 1641.

It will be obvious to one skilled in the art that alternative data acquisition systems, other than the one described above, may be designed. In one embodiment for example all the detectors may communicate with a single signal processor block.

Figure 17:
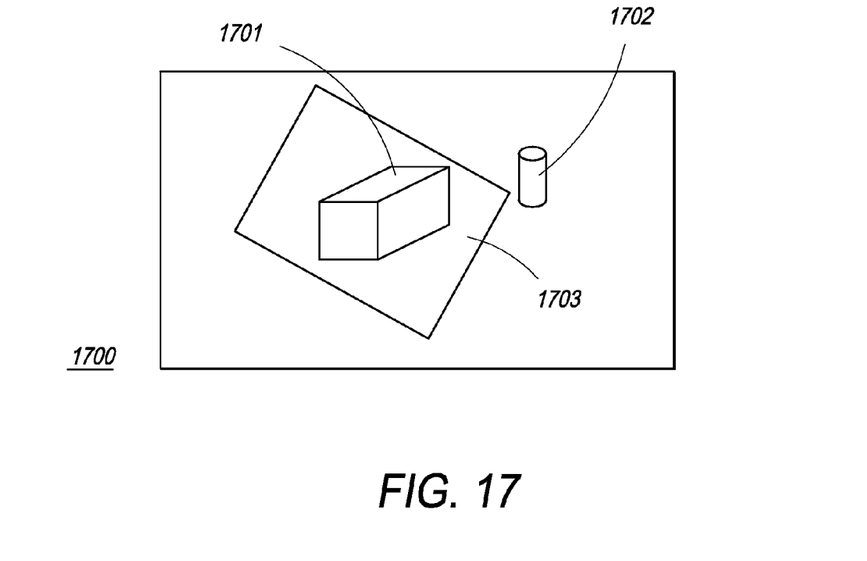
FIG. 17 illustrates an exemplary three-dimensional image obtained by using the time of flight backscatter imaging system of the present invention.

The time profile data generated by the detectors and signal processor units as shown in FIG. 16 contains both depth and material type information. This data may be rendered to a display as a three dimensional image where the shape of the rendered image is derived from the position of the time step pulses in the corrected time profile while grey-scale value is derived from the height of each step pulse in the corrected time profile. In one method used by the system of present invention, the heights of step pulses are corrected for distance from the source by application of the inverse square law. The heights of time steps are also corrected for self-attenuation of the backscattered beam by overlapping objects. An example of a three-dimensional time of flight backscatter image rendered as described above is shown in FIG. 17. Referring to FIG. 17, in the image 1700 on display, a rectangular object 1701 and a cylindrical object 1702 can be seen behind a planar skin 1703. It may be noted that both grey-scale and pseudo-colour tables can be used to represent image data on the screen.

To display the time of flight backscatter data, each measurement is associated with a position in a 3D volume. The position of a signal is first mapped into a 2D radial grid whose origin is at the X-ray tube focus and whose plane is described by the rotation of the collimator. This radial grid may then be interpolated into an equivalent 2D Cartesian grid. As the object is scanned past the X-ray beam, a series of 2D images are obtained which together form a 3D image of the object under inspection. The 3D Cartesian grid may then be rendered to a computer screen using standard ray-tracing methods with suitable transparency and coloring as required by the operator.

While it is known that time of flight calculations are used across many different industries, for example, IR systems use time of flight to calculate object distances, there are complications to such uses. For example in using time of flight in ultrasound B-scan, the velocity of sound is much lower than velocity of light, so electronics can be much slower. Here one can get attenuation and reflection by overlapping objects whereas in X-ray systems there is attenuation only. In laser range finder applications, one looks for the leading edge of the pulse only without unscrambling the leading edge profile, since the attenuation of the length of light in reflective materials is relatively small. In the X-ray case, however, there is a substantial amount of information in the shape profile, and this is what makes the X-ray system very different (more complex but powerful) than the optical case. In radar applications, one only looks for the time of arrival of the leading edge of the pulse only with some information contained in the intensity (corrected of course for distance from the source). Note that the leading edge profile is not used since the wavelength of radio waves is generally large compared to the size of the object of interest and therefore there is little depth information to be obtained.

This time of flight backscatter system provides the ability to take into account and measure the surface and sub-surface profile of an object under inspection. This capability is advantageous as it allows the production of dimensionally accurate images, such that, for example, an object or a person does not appear larger or smaller than its actual size. The screening and imaging method of the present invention further provides for much deeper inspection than is provided by currently available backscatter systems. The time of flight backscatter system of the present invention also offers the capability of three-dimensional display of backscatter data with a much improved level of material characterization, compared to existing systems.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. An X-ray imaging apparatus for determining a surface profile of an object under inspection and positioned at a distance from said apparatus, comprising:
   a flying spot X-ray source for producing a flying spot scanning beam of X-rays directed toward said object;
   a transmission imaging system comprising a pulsed linear accelerator X-ray source;
   a detector assembly adapted to provide a signal representative of an intensity of X-rays backscattered from said object;
   processing circuitry adapted to determine a time difference between when the flying spot X-ray source is switched on and when the backscattered X-rays arrive at the detector assembly and adapted to output data representative of the surface profile of the object under inspection; and
   processing circuit adapted to operate the pulsed linear accelerator X-ray source only when said flying spot scanning beam is not interacting with said object.

2. The X-ray imaging apparatus of claim 1 wherein a minimum distance between the apparatus and the object under inspection is 100 mm.

3. The X-ray imaging apparatus of claim 1 wherein a maximum distance between the apparatus and the object under inspection is 5 m.

4. The X-ray imaging apparatus of claim 1 wherein the flying spot X-ray source is pulsed such that a duration of the flying spot X-ray beam being on is in the range of 1μs to 100 μs and a duration of the flying spot X-ray beam being off is in the range of 1 μs to 100μs.

5. The X-ray imaging apparatus of claim 1 wherein a duration of the flying spot X-ray beam on time and off time is each less than 1 ns.

6. The X-ray imaging apparatus of claim 1 wherein the flying spot X-ray source is mounted on a vehicle which is adapted to be driven past the object under inspection.

7. The X-ray imaging apparatus of claim 1 wherein the flying spot X-ray source is mounted on a vehicle that is adapted to be driven to an inspection site and kept stationary while the object under inspection passes the vehicle.

8. A portal gantry having a top side, left side, and right side, comprising the X-ray imaging apparatus of claim 1.

9. The portal gantry of claim 8 wherein the X-ray imaging apparatus is integrated into at least two of the top side, left side, or right side.

10. An X-ray imaging apparatus for determining the presence and location of a threat beneath an exterior surface of an object under inspection, comprising:
    a pencil beam X-ray source for producing a scanning pencil beam of X-rays directed toward said object;
    a transmission imaging system comprising a pulsed linear accelerator X-ray source;
    a detector assembly adapted to provide a first signal representative of an intensity of the X-rays backscattered from said exterior surface of the object under inspection and a second signal representative of an intensity of the X-rays backscattered from said threat beneath the exterior surface of the object under inspection;
    processing circuitry adapted to determine a first time difference between when the pencil beam X-ray source is switched on and when the X-rays backscattered from the exterior surface of the object under inspection arrive at the detector assembly and a second time difference between when the pencil beam X-ray source is switched on and when the X-rays backscattered from the threat beneath the exterior surface of the object under inspection arrive at the detector assembly and adapted to output data representative of a surface profile of the object under inspection based upon at least one of said first time difference or second time difference; and
    processing circuitry adapted to operate the pulsed linear accelerator X-ray source only when said scanning pencil beam is not interacting with said object.

11. The X-ray imaging apparatus of claim 10 wherein a minimum distance between the apparatus and the object under inspection is 100 mm.

12. The X-ray imaging apparatus of claim 10 wherein a maximum distance between the apparatus and the object under inspection is 5 m.

13. The X-ray imaging apparatus of claim 10 wherein the pencil beam X-ray source is pulsed such that a duration of the scanning pencil beam being on is in the range of 1 μs to 100 μs and a duration of the scanning pencil beam being off is in the range of 1μs to 100 μs.

14. The X-ray imaging apparatus of claim 10 wherein a duration of the scanning pencil beam on time and off time is each less than 1 ns.

15. The X-ray imaging apparatus of claim 10 wherein the pencil beam X-ray source is mounted on a vehicle which is adapted to be driven past the object under inspection.

16. The X-ray imaging apparatus of claim 10 wherein the pencil beam X-ray source is mounted on a vehicle that is adapted to be driven to an inspection site and kept stationary while the object under inspection passes the vehicle.

17. A method for determining a surface profile of an object under inspection, said method comprising the steps of:
   positioning the object under inspection at a distance from an X-ray imaging apparatus, wherein said X-ray imaging apparatus comprises a backscatter X-ray source and a detector array and further comprises a transmission X-ray source;
   operating said backscatter X-ray source to produce a scanning pencil beam of X-rays directed toward said object;
   operating said transmission X-ray source to produce a beam of X-rays directed toward said object only when said backscatter X-ray source is not operating;
   detecting a signal representative of an intensity of the X-rays backscattered from said object, using said detector array;
   determining a time difference between when the backscatter X-ray source is switched on and when the backscattered signal is detected; and
   outputting data representative of the surface profile of the object under inspection.

18. The method of claim 17 wherein the object under inspection is positioned no closer than 100 mm and no farther than 5 m from the X-ray imaging apparatus.

19. The method of claim 17 wherein the backscatter X-ray source is kept on for no less than 1 μs and no more than 100 μs and is kept off for no less than 1 μs and no more than 100 μs.

20. The method of claim 17 wherein the backscatter X-ray source is kept on for less than 1 ns and kept off for less than 1 ns.

* * * * *